United States Patent [19]

Segre

[11] Patent Number: 5,377,838
[45] Date of Patent: Jan. 3, 1995

[54] FLEXIBLE CONTAINER FOR WASHING AND IN-SERVICE INTEGRATION OF DIALYSIS CIRCUITS AND FILTERS

[75] Inventor: Ariel D. Segre, Milan, Italy

[73] Assignee: S.I.F. RA. Societa Italiana Farmaceutical Ravizza S.p.A., Italy

[21] Appl. No.: 157,752

[22] Filed: Nov. 24, 1993

[51] Int. Cl.⁶ .............................................. B65D 30/22
[52] U.S. Cl. .................................. 206/527; 134/201; 206/484; 221/94; 383/38
[58] Field of Search ................. 134/99.1, 186, 201; 206/216, 219, 223, 568, 484, 527; 221/94, 478, 481, 564; 383/38, 40; 604/410

[56] References Cited

U.S. PATENT DOCUMENTS

| | | |
|---|---|---|
| 3,304,977 | 2/1967 | Hammons ............................ 383/38 |
| 4,403,992 | 9/1983 | Bertellini et al. ................... 604/410 |
| 4,467,588 | 8/1984 | Carveth ............................... 206/219 |
| 4,810,376 | 3/1989 | Magasi ................................. 210/136 |
| 4,955,508 | 9/1990 | Capanna et al. ...................... 222/94 |
| 4,997,083 | 3/1991 | Loretti et al. ....................... 206/219 |

FOREIGN PATENT DOCUMENTS

| | | |
|---|---|---|
| 1209560 | 8/1989 | Italy . |
| 0598067 | 4/1978 | Switzerland ........................ 383/78 |

Primary Examiner—Jimmy G. Foster
Attorney, Agent, or Firm—Quarles & Brady

[57] ABSTRACT

A flexible container featuring at least two chambers, each containing a predetermined amount of physiological solution for washing the extracorporeal, blood-side circuit of dialysis equipment; a first chamber being U-shaped, and the second chamber being located axially inwards of the first chamber.

4 Claims, 2 Drawing Sheets

FLEXIBLE CONTAINER FOR WASHING AND IN-SERVICE INTEGRATION OF DIALYSIS CIRCUITS AND FILTERS

BACKGROUND OF THE INVENTION

The present invention relates to a container or bag for supplying detergent or wash solution to the circuits and filters of dialysis equipment.

For dialysis applications, increasing use has been made over the past few years of disposable single-cycle plastic circuits and filters.

This applies in particular to those parts of the dialysis equipment coming into contact with the patient's blood.

Such circuits and filters are made of appropriate plastic material and, prior to use, i.e. before being connected to the patient's circulation system, must be washed using a physiological (e.g. 0.9% NaCl) solution for eliminating even minor traces of substances used in the manufacture, completion and, particularly, sterilization of the circuits and filters (such as glycerine, ethylene oxide, etc.).

This is not only advisable from the therapeutic standpoint—in that even minor traces of such substances may possibly be toxic and at any rate are certainly to be avoided in the case of patients subjected to a blood purifying process—but is also prescribed by specific health regulations.

Italian Patent n. 1-209.560, issued on 30 August, 1989 to Pierrel Hospital Spa and subsequently transferred to the present Applicant, relates to a container for supplying a wash solution to the circuits and filters of dialysis equipment.

The same patent, which forms an integral part of the present description and to which full reference is made herein in the interest of full disclosure, also relates to a special washing method, and to a number of alternative extracorporeal circuits to which the method also applies.

In particular, the above patent relates to a container for performing the above functions, and comprising two side side, independent, noncommunicating chambers connectable to the extracorporeal circuit on the blood side of the dialysis equipment.

A first chamber contains a certain amount of physiological solution which is circulated continuously in the circuit and back to the first chamber.

This provides for a first wash cycle for removing any toxic substances contained in the circuit.

Subsequently, a certain amount of fresh physiological solution is withdrawn from the second chamber and fed into the circuit for the final wash cycle.

At this point, the circuit is ready for connection to the patient.

To prevent the physiological solution from stagnating inside the first chamber, this is provided inside with a partition extending from the base of the container towards the opposite portion, to a point roughly halfway up the chamber, and located between two inlet/drain fittings connected to the circuit, so as to form a compulsory path for the physiological solution circulating in the first chamber.

Though generally successful, the above partition solution fails to provide for eliminating stagnation under certain extreme circumstances (involving, for example, a fairly high content of toxic substances in the circuit, or due to the nature of the toxic substances or the speed at which the physiological solution is circulated inside the chamber).

SUMMARY OF THE INVENTION

It is an object of the present invention to further reduce the possibility of such stagnation.

According to the present invention, there is provided a flexible container of plastic material for washing and in-service integration of extracorporeal blood circulating circuits and filters of dialysis equipment, said container comprising at least a first sealed chamber containing a first predetermined quantity of physiological saline solution; and at least a second sealed chamber containing a second predetermined quantity of physiological saline solution; said first and second chambers being independent and noncommunicating fluidically; said first chamber presenting two inlet and drain fittings connectable fluidically to said circuit; and said second chamber presenting a single inlet and drain fitting connectable fluidically to said circuit; characterized by the fact that said first chamber is in the form of an upside down U with axially spaced arms extending from said two fittings towards the opposite part of the container, where they are connected by a curved portion; said second chamber being located axially between said arms of said first chamber and extending from said single fitting towards the opposite part of the container; and said first and second chambers being separated by at least one hermetic heat seal.

According to a preferred embodiment, the container is made of transparent thermoplastic material, and said first and second chambers are adjacent to each other.

According to a further preferred embodiment, the container comprises a third sealed, normally empty chamber with an inlet and drain fitting connectable fluidically to said circuit; said third chamber being externally adjacent to one arm of said first chamber, and being separated from said arm by at least one hermetic heat seal.

BRIEF DESCRIPTION OF THE DRAWINGS

A preferred, non-limiting embodiment of the present invention will be described by way of example with reference to the accompanying drawings, in which.

DETAILED DESCRIPTION OF THE INVENTION

Figure 1:
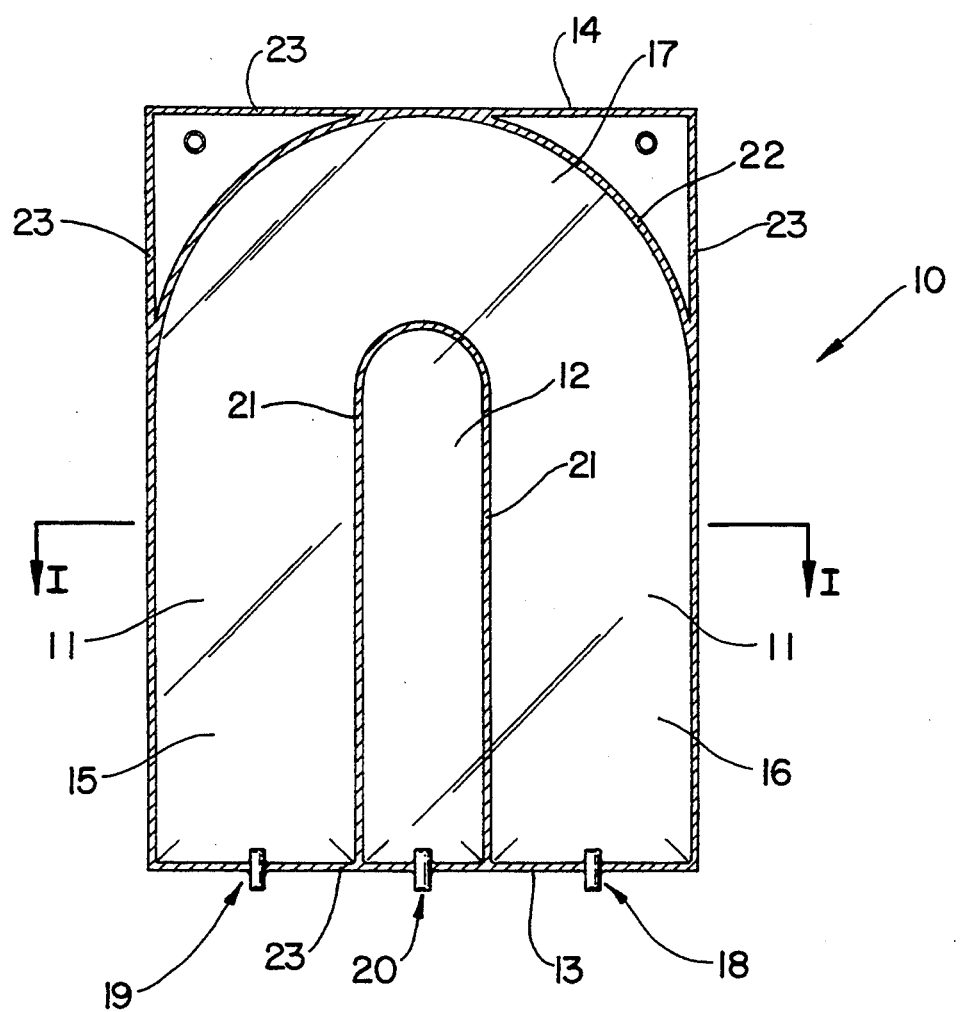
FIG. 1 shows a section of a container in accordance with the present invention.

Number 10 in FIG. 1 indicates a container in the form of a flexible bag made of plastic, preferably transparent material, and in which are defined two independent, fluidtight, hydraulically noncommunicating chambers 11 and 12. Chamber 11 extends from the base 13 to the top 14 of the container, and is in the form of an upside down U, the arms 15 and 16 of which are axially spaced and connected by a curved portion 17.

At base 13 of the container, chamber 11 presents two inlet/drain fittings 18, 19 connectable to the extracorporeal blood circulating circuit (FIG. 3) of dialysis equipment, the structure of which is described later on.

Fittings 18, 19 present breakoff caps (for sterility and optimum flow) and adjustable valves which may be opened and closed as required and of the type used, for example, on phleboclysis tubes.

Arms 15, 16 and curved portion 17 of chamber 11 preferably present a substantially constant cross section.

Chamber 12 is located axially inmost in relation to chamber 11, i.e. between arms 15 and 16, and extends from base 13 towards the opposite part of the container and to curved portion 17.

The height of chamber 12 is roughly equal to or greater than half the maximum height of chamber 11.

Though shown adjacent to each other, chambers 11, 12 may be spaced slightly apart, while at the same time maintaining, of course, the overall configuration described above.

At base 13, chamber 12 presents an inlet/drain fitting 20 connectable to the extracorporeal blood circulating circuit (FIG. 3) of dialysis equipment.

Figure 2:
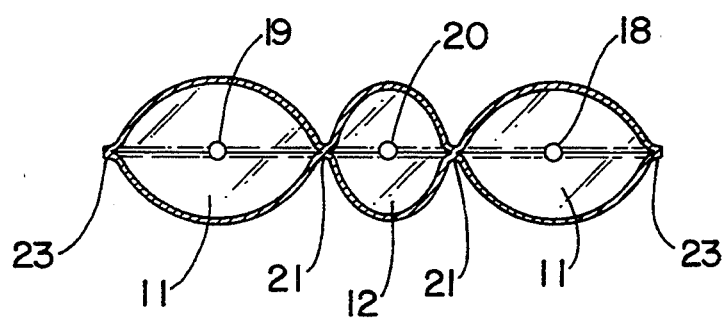
FIG. 2 shows a section along line I—I of the FIG. 1 container.

As shown also in FIG. 2, chambers 11, 12 are separated by a hermetic heat seal 21 which, for improved sealing performance, preferably consists of two preferably parallel heat seals.

Similar heat seals define the outer curve 22 of portion 17 and edges 23 of container 10.

Figure 3:
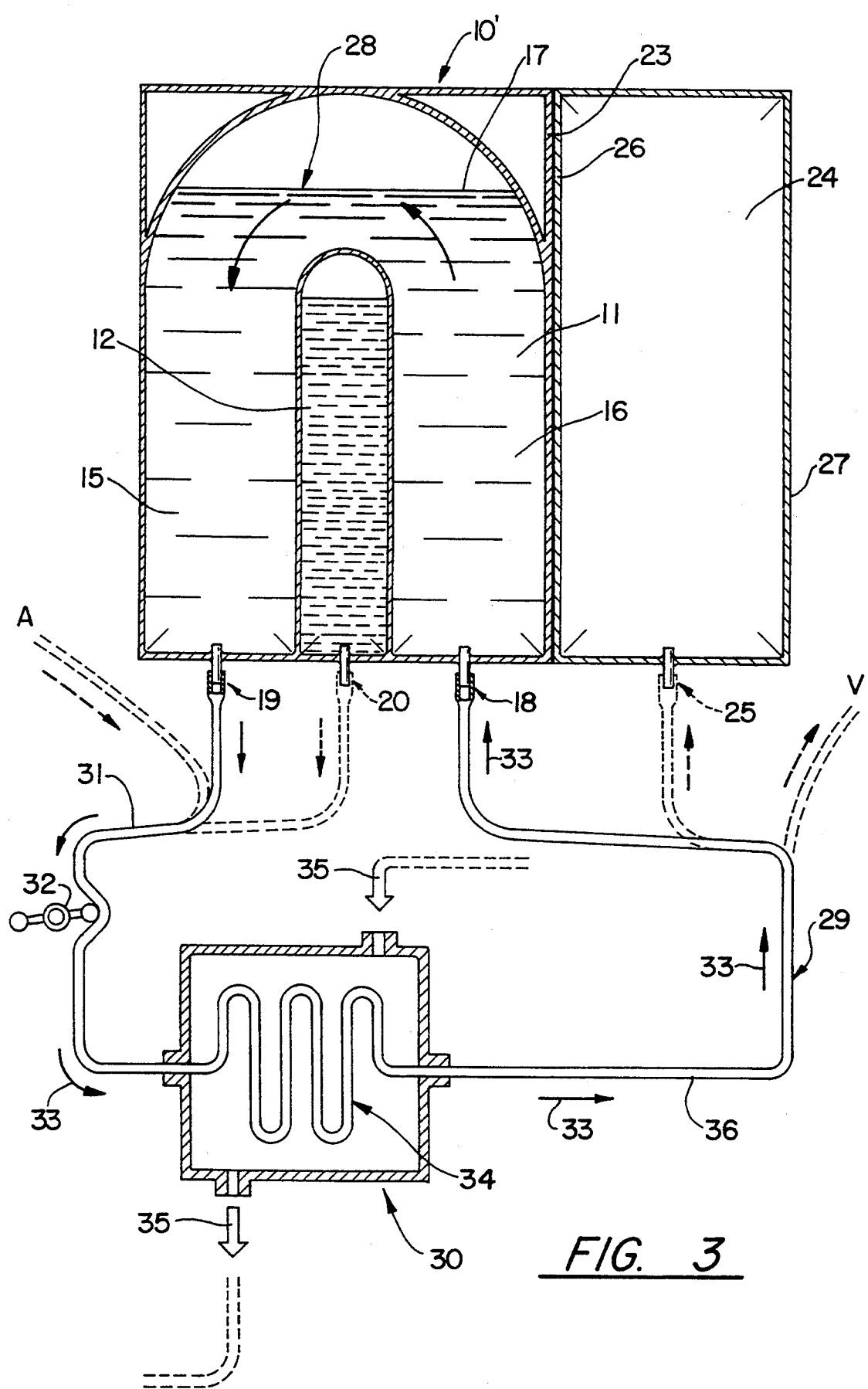
FIG. 3 shows a section of a further embodiment of a container in accordance with the present invention and connected to an example circuit shown schematically.

FIG. 3 shows a container 10' similar to that in FIG. 1 but which presents an additional sealed chamber 24 with an inlet/drain fitting 25 connectable to the extracorporeal blood circulating circuit of dialysis equipment and having the same characteristics as fittings 18, 19, 20 in FIG. 1.

Chamber 24 is located adjacent to arm 16 of chamber 11 and to the corresponding edge 23 of container 10', and chambers 24 and 11 are separated by a double hermetic heat seal 26.

Similarly, edges 27 are also defined by hermetic heat seals.

As can be seen, chamber 11 contains a certain amount of physiological saline solution up to level 28 for enabling chamber 11 to receive an additional amount of liquid; while chamber 12 is filled with a certain amount of physiological saline solution to which other substances, such as drugs for sustaining the blood pressure of the patient, may be added.

Chamber 24 on the other hand is empty for receiving the used physiological saline solution downstream from circuit 29.

FIG. 3 shows a schematic view of the extracorporeal circuit 29 on the blood side, incorporating dialysis unit 30 and to which container 10 or 10' is connectable by means of fittings 18, 19, 20 and 25.

The circuit comprises a first branch 31 connectable to fitting 19 or 20 and featuring a pump 32, e.g. a roller type, for pumping and effecting circulation in the direction of arrows 33.

Dialysis unit 30 containing a semipermeable membrane type filter 34 presents inlet and outlet fittings for the dialytic solution as indicated by arrows 35.

The outlet of unit 30 presents a second branch 36 connectable to fitting 18 or 25 (in the event chamber 24 is provided).

The physiological saline wash solution in chamber 11 flows through fitting 19 and, with the aid of pump 32, along circuit 29 in the direction of arrows 33, and back to chamber 11 along branch 36 and through fitting 18.

Dialytic solution circuit 35 is closed.

The physiological solution then flows up arm 16, along curved portion 17, down arm 15 and back to circuit 29 for the next cycle.

Hence, any toxic substances in the circuit are removed and fed into chamber 11.

After washing, fitting 19 is closed; branch 31 is connected to fitting 20 of chamber 12 (as shown by the dotted line in FIG. 3); and the fresh physiological solution in chamber 12 ks fed into circuit 29 and, with the aid of pump 32, pushes the physiological wash solution in the direction of arrows 33 and into chamber 11 through fitting 18.

Both the physiological wash solution and the fresh solution are thus collected in chamber 11.

At this point, fitting 18 is closed to disconnect container 10; and branches 31 and 36 of the circuit are connected respectively to points A and V of the patient's artery and vein system.

At the same time, dialytic solution circuit 35 is opened.

The above operations apply to the FIG. 1 container 10 comprising chambers 11 and 12. As regards the FIG. 3 container 10' featuring an additional chamber 24, circuit 29 is washed in substantially the same way except that, instead of being fed back into chamber 11, both the physiological wash solution and the fresh solution are fed along branch 36 and through fitting 25 into chamber 24, as shown by the dotted line in FIG. 3.

In containers 10 and 10' as described above, therefore, curved portion 17 hydraulically connecting arms 15 and 16 of chamber 11 provides for eliminating any corners or "dead areas" in the chamber, thus eliminating the formation of stagnant physiological wash solution.

To those skilled in the art it will be clear that changes may be made to the preferred embodiments described and illustrated herein without, however, departing from the scope of the present invention.

I claim:

1. A flexible container of plastic material for washing and in-service integration of extracorporeal blood circulating circuits and filters of dialysis equipment, said container comprising at least a first sealed chamber containing a first predetermined quantity of physiological saline solution; and at least a second sealed chamber containing a second predetermined quantity of physiological saline solution; said first and second chambers being independent and noncommunicating fluidically; said first chamber presenting two inlet and drain fittings connectable fluidically to said circuit; and said second chamber presenting a single inlet and drain fitting connectable fluidically to said circuit; characterized by the fact that said first chamber is in the form of an upside down U with axially spaced arms extending from said two fittings towards the opposite part of the container, where they are connected by a curved portion; said second chamber being located axially between said arms of said first chamber and extending from said single fitting towards the opposite part of the container; and said first and second chambers being separated by at least one hermetic heat seal.

2. A container as claimed in claim 1, characterized by the fact that said first and second chambers are adjacent to each other.

3. A container as claimed in claim 1, characterized by the fact that it is made of transparent thermoplastic material.

4. A container as claimed in claim 1, characterized by the fact that it comprises a third sealed, normally empty chamber with an inlet and drain fitting connectable fluidically to said circuit; said third chamber being externally adjacent to one arm of said first chamber, and being separated from said arm by at least one hermetic heat seal.

* * * * *